United States Patent [19]

Bremus et al.

[11] 4,381,407

[45] Apr. 26, 1983

[54] PROCESS FOR THE CONTINUOUS PRODUCTION OF TRIACETIN

[75] Inventors: Norbert Bremus, Langenfeld; Gerhard Dieckelmann, Hilden; Lutz Jeromin, Düsseldorf-Holthausen; Wolfgang Rupilius, Düsseldorf-Urdenbach; Hartwig Schütt, Düsseldorf-Benrath, all of Fed. Rep. of Germany

[73] Assignee: Henkel Kommanditgesellschaft auf Aktien, Düsseldorf-Holthausen, Fed. Rep. of Germany

[21] Appl. No.: 228,452

[22] Filed: Jan. 26, 1981

[30] Foreign Application Priority Data

Feb. 8, 1980 [DE] Fed. Rep. of Germany ....... 3004660

[51] Int. Cl.$^3$ .................... C07C 67/08; C07C 67/54; C07C 69/18
[52] U.S. Cl. .................................. 560/263; 202/158; 203/DIG. 6; 560/248; 562/607; 562/608
[58] Field of Search ............... 202/158; 560/263, 248; 562/607, 608; 203/DIG. 6, 16

[56] References Cited

U.S. PATENT DOCUMENTS 3,674,839  7/1972  Vogt et al. ......................... 560/263
3,776,948  12/1973  Kleemann et al. ................. 560/263

*Primary Examiner*—Vivian Garner
*Attorney, Agent, or Firm*—Hammond & Littell, Weissenberger and Muserlian

[57] ABSTRACT

A process for the continuous production of triacetin consisting essentially of continuously charging liquid glycerol into a first liquid reaction area through which acetic acid vapors and water vapors flow, said liquid reaction area being divided into a number of separate individual areas through which liquid glycerol and liquid acetin reaction products flow in one direction and gaseous acetic acid and water flow in a countercurrent direction, continuously charging acetic acid vapor to a separate individual area where said liquid mixture has an OH number of less than 600, continuously separating a liquid mixture of acetins and water having an OH number of less than 600, continuously passing said liquid mixture into a second liquid reaction area, continuously adding thereto liquid acetic acid anhydride in an amount sufficient to react with water dissolved in said liquid mixture to form acetic acid and to react with monoacetin and diacetin present to form triacetin and continuously recovering triacetin.

10 Claims, 7 Drawing Figures

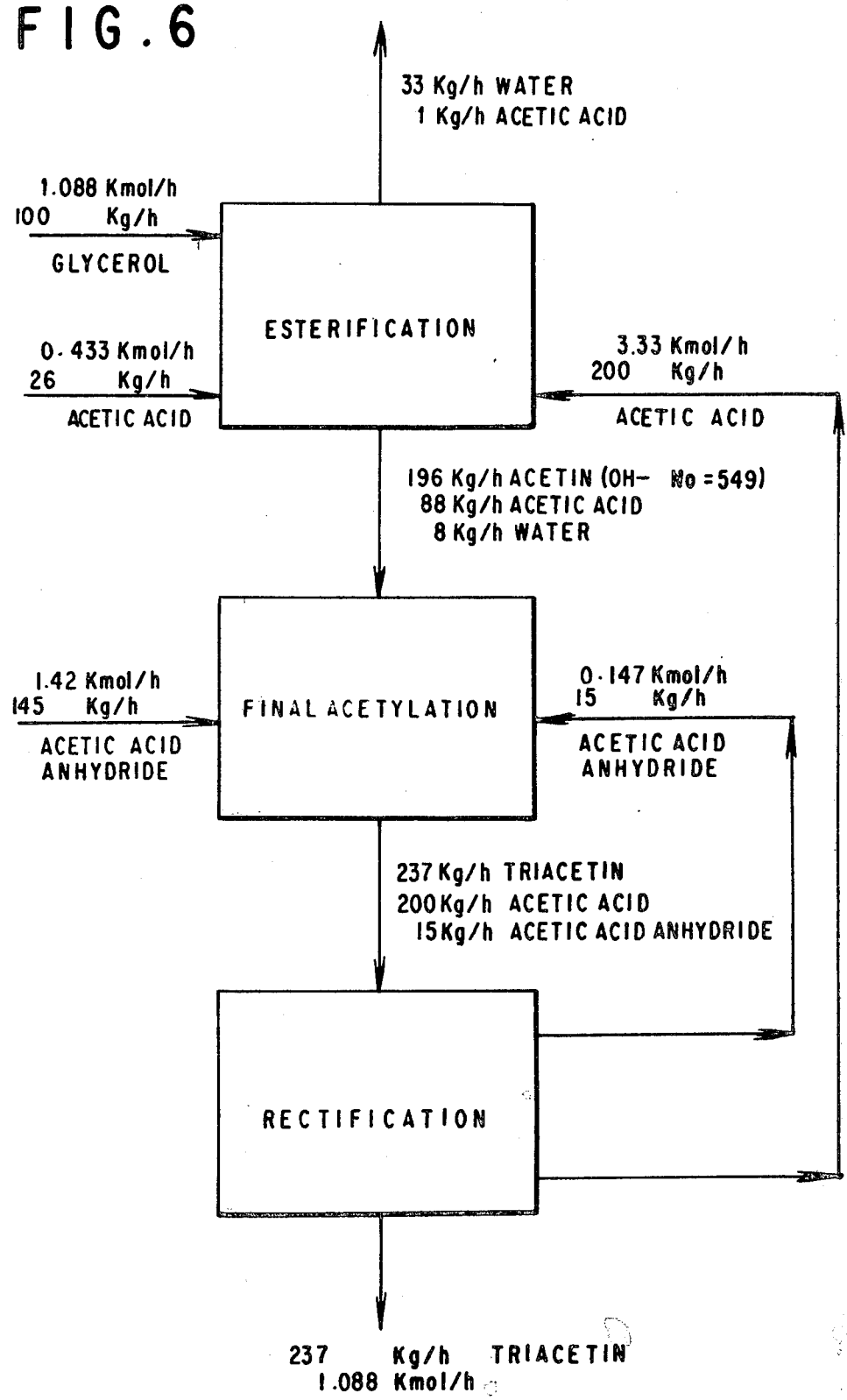

PROCESS FOR THE CONTINUOUS PRODUCTION OF TRIACETIN

BACKGROUND OF THE INVENTION

This invention relates to a continuous process for the preparation of triacetin from glycerol, acetic acid and acetic acid anhydride.

A discontinuous process for the preparation of triacetin in which glycerol and acetic acid anhydride in a molar ratio of 1:3 are reacted at 130° C. to 135° C., is known from German Patent Specification DE-PS No. 347,897. In this reaction, for each mol of reacted glycerol, 3 mols of acetic acid are produced for which there is generally hardly any way of utilization, making this method unsuitable for the large-scale production of triacetin.

Also known are discontinuous methods for the preparation of triacetin from glycerol and acetic acid, as can be learned from the journal, Seifen-Öle-Fette-Wachse, 1962, pp. 597–602. Since the reaction equilibrium is on the side of the starting materials in this reaction, the water produced during the esterification reaction must be removed continuously from the reaction mixture to keep the required acetic acid to a reasonable amount. These methods require long reaction times and therefore have a high energy consumption and a poor utilization of the reactor capacity.

As can be seen from Seifen-Öle-Fette-Wachse, 1962, p. 598, the esterification reaction can be accelerated, especially in the low temperature range from 100° to 160° C., by acid catalysts. The catalyst must have a lower vapor pressure than glycerol to prevent its accumulation in the vapor phase.

In addition, German Published Application DE-OS 19 05 880 describes the production of triacetin from the reaction of allyl acetate with acetic acid and acetic acid anhydride in the presence of a catalyst. Now it was found that the disadvantages of the known methods can be largely eliminated by using the continuous process for the preparation of triacetin described below.

OBJECTS OF THE INVENTION

An object of the present invention is the development of a continuous process for the production of triacetin from glycerol, acetic acid and acetic acid anhydride wherein only small amounts of acetic acid are removed unreacted.

Another object of the present invention is the development of a process for the continuous production of triacetin consisting essentially of continuously charging liquid glycerol into a first liquid reaction area through which acetic acid vapors and water vapors flow, said liquid reaction area being divided into a number of separate individual areas through which liquid glycerol and liquid acetin reaction products flow in one direction and gaseous acetic acid and water flow in a countercurrent direction, continuously charging acetic acid vapor to a separate individual area where said liquid mixture has an OH number of less than 600, said liquid reaction areas being maintained at a pressure of from 0.2 to 30 bar and a temperature of from 100° to 250° C., the number of said separate individual areas and the amount of liquid glycerol and gaseous acetic acid charged being so selected that the total contact time of the reactants is at least one hour, continuously separating a liquid mixture of acetins and water having an OH number of less than 600, continuously passing said liquid mixture into a second liquid reaction area, continuously adding thereto liquid acetic acid anhydride in an amount sufficient to react with water dissolved in said liquid mixture to form acetic acid and to react with monoacetin and diacetin present to form triacetin, continuously recovering triacetin, continuously passing vaporized acetic acid formed into said separate individual area where said liquid mixture has an OH number of less than 600, and continuously recovering a mixture of water vapors and acetic acid vapors having a content after condensation of less than 3% by weight of acetic acid.

These and other objects of the invention will become more apparent as the description thereof proceeds.

THE DRAWINGS

FIG. 6 shows a block flow diagram of one embodiment of the invention;

DESCRIPTION OF THE INVENTION

Figure 1:
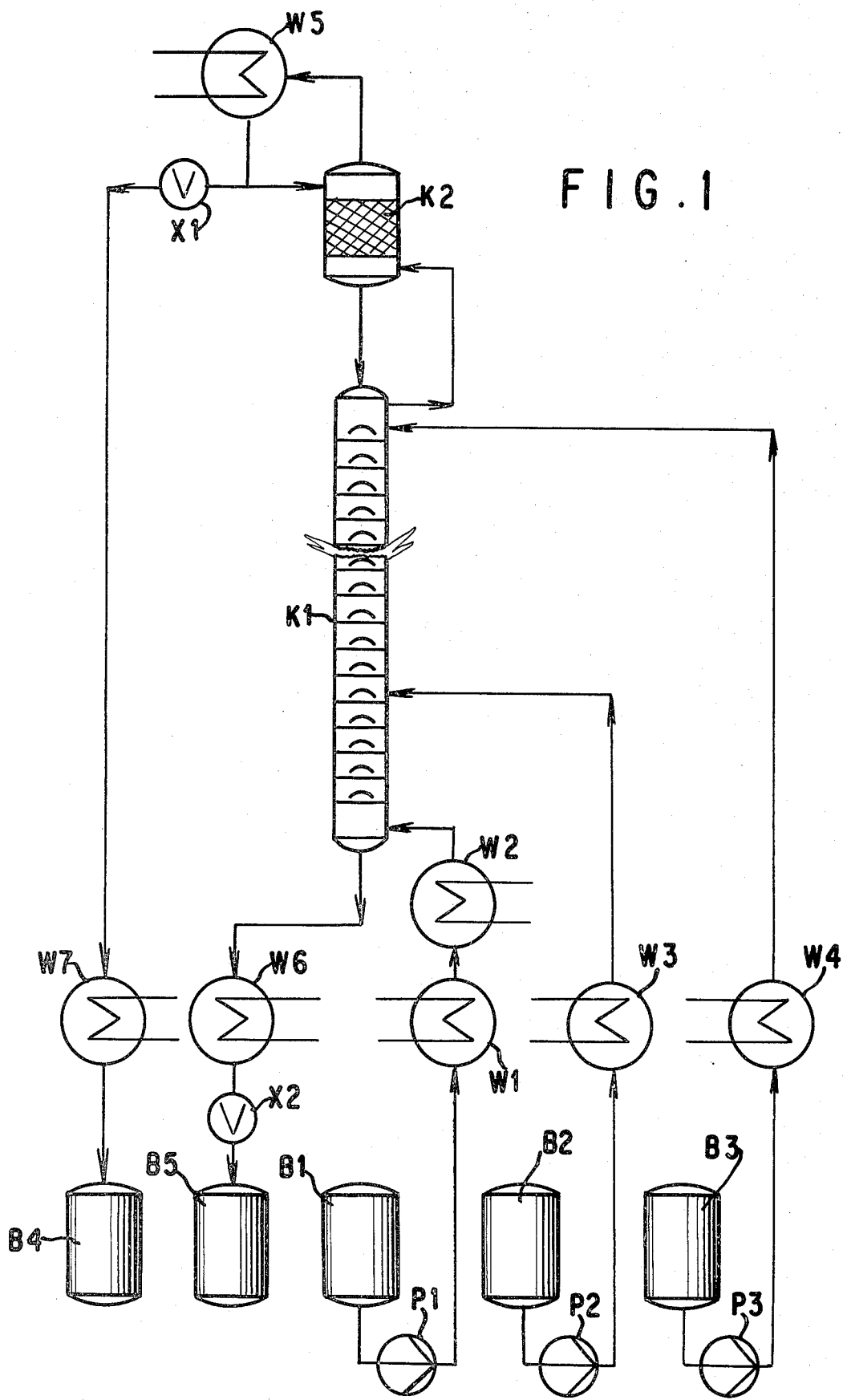
FIG. 1 shows a flow diagram for the continuous production of triacetin.

The subject of the invention is a continuous process for the preparation of triacetin by the reaction of glycerol with acetic acid and acetic acid anhydride at elevated temperature and, optionally, in the presence of catalysts, which is characterized in that the reaction partners are reacted with each other in a continuous countercurrent process, for which purpose liquid glycerol is inserted in an ascending stream of superheated acetic acid vapor at a pressure of 0.2 to 30 bar and a temperature of 100° to 250° C. in an esterification column with a number of plates, the reaction time of the liquid reaction mixture amounting to at least one hour and acetic acid anhydride is added to the descending reaction mixture upon reaching an OH-number of less than 600 at the respective plate of the reaction column or in a correspondingly designed second reactor, in an amount that the water dissolved at this point in the reaction phase can be converted quantitatively into acetic acid and the monoacetin and diacetin present can be converted into triacetin.

More particularly, the present invention relates to a process for the continuous production of triacetin consisting essentially of continuously charging liquid glycerol into a first liquid reaction area through which acetic acid vapors and water vapors flow, said liquid reaction area being divided into a number of separate individual areas through which liquid glycerol and liquid acetin reaction products flow in one direction and gaseous acetic acid and water flow in a countercurrent direction, continuously charging acetic acid vapor to a separate individual area where said liquid mixture has an OH number of less than 600, said liquid reaction areas being maintained at a pressure of from 0.2 to 30 bar and a temperature of from 100° to 250° C., the number of said separate individual areas and the amount of liquid glycerol and gaseous acetic acid charged being so selected that the total contact time of the reactants is at least one hour, continuously separating a liquid mixture of acetins and water having an OH number of less than 600, continuously passing said liquid mixture into a second liquid reaction area, continuously adding thereto liquid acetic acid anhydride in an amount sufficient to react with water dissolved in said liquid mixture to form acetic acid and to react with monoacetin and diacetin present to form triacetin, continuously recovering triacetin, continuously passing vaporized acetic acid formed into said separate individual area where said liquid mixture has an OH number of less than 600, and continuously recovering a mixture of water vapors and acetic acid vapors having a content after condensation of less than 3% by weight of acetic acid.

When the process takes place in the absence of catalysts, the reaction pressure preferably lies in the range from 3 to 30 bar and the reaction temperature in the range from 180° to 250° C. In the presence of catalysts, the reaction pressure can be lower and preferably from 0.2 to 3 bar and the reaction temperature is likewise lower, preferably from 100° to 180° C.

Acid esterification catalysts are suitable for the process according to the invention, particularly p-toluene sulfonic acid, concentrated sulfuric acid, trifluoroacetic acid, potassium hydrogen sulfate, aluminum sulfate or zinc acetate. The use of p-toluenesulfonic acid as catalyst is preferred. The amount of catalyst, based on the amount of glycerol used, is 0.01% to 0.5% by weight. More particularly, therefore, the reaction can be conducted in the presence of from 0 to 0.5% by weight of an acid esterification catalyst, based on the amount of glycerol charged. The acid esterification catalyst is charged with the glycerol.

Glycerol with an OH number of 1,828 is preferably used for the process according to the invention. Acetic acid is used in a molar ratio to glycerol of 2.5:1 to 5:1. The amount of acetic acid anhydride that is added to the reaction mixture in the lower third of the column, or in the second reactor, is 0.1 to 1.5 mol per mol of glycerol to be converted.

The preparation of triacetin by the process according to the invention takes place advantageously in the equipment for the liquid-vapor reactions described below. The equipment consists of a reaction column with a rectifying column added on the top, heat exchangers, storage containers, feeding pumps and connecting pipelines.

The reaction column is in the form of a bubble plate column with at least 20 double bubble plates. The inner bubble is needed for the adjustment of the dry pressure loss and for the immersion of the intake tube of the plate above during the starting of the column. The outer bubble serves for the distribution of the vapor in the liquid and provides the exchange surface for the substances. The entire surface of the bubbles on one plate amounts to 10% to 30% of the surface lying between the intake and outlet weir. The vapor penetration area through the bubbles set on the plates amounts to 0.3% to 3% of the inside column cross-section. The vapor penetration surface is distributed over at least 4 orifices per bubble. The orifices have a diameter of 2 to 5 mm and are located on the periphery of the outer bubbles, 5 to 20 mm above the plate. The height of the outlet tube is at least 80 mm above the bubble plate.

This construction of the bubble plate column permits an extremely high liquid level on the plates at a low vapor load, resulting in the long contact time required for the performing of the esterification. The construction and arrangement of the bubbles leads to a uniform distribution of the vapor phase over the effective column cross-section, reduces pulsating liquid currents and lends a high rate of flow to the vapor upon emergence from the bubble. It is recommended that the vapor penetration area be so selected that when air is passed through, its velocity is about 4 to 30 meters per second, preferably 15 meters per second, in order to facilitate the mixing of the reaction partners.

A suitable construction of the cross-sections for the penetration of the vapor through the bubbles consists of at least 4 vertical slits with a width of 2 to 5 mm and a height of 5 to 20 mm, arranged in the bubble close to the plate, instead of the circular orifices. With the high liquid levels on the plates and the low vapor loads, each slit is filled with vapor only to a small extent, while the remaining lower part of the slits is closed by the liquid standing on the plate. The slits have the advantage over the orifices in that they clog less easily. In addition, a larger penetration area always is automatically available when larger amounts of vapor are present, since the vapor can blow open a larger cross-section, if necessary. It is also advantageous that the intake and outlet weirs have at least the height of the outlet tube that determines the level of the liquid and that they have slits close to the plate, through which the liquid can flow in and drain out. Another suitable part of the construction is a diaphragm in the neck of the inner bubble with an orifice of 2 to 15 mm.

For larger column plates (diameter exceeding 300 mm), the liquid gradient forming more strongly on the plate must be taken into consideration for the configuration of the bubbles. A uniform distribution of the vapor over all bubbles of the plate is guaranteed only when the so-called dry pressure loss of the plate (which is measured when the plate is penetrated by the vapor and no liquid remains on it) is at least twice as great as the hydrostatic difference in height between intake and outlet caused by the liquid gradient. The necessary dry pressure loss can be achieved by building a diaphragm with an orifice of 2 to 15 mm diameter into the neck of the inner bubble. The effectively necessary size of the diaphragm can be determined by a simple experiment. The dry pressure loss also can be obtained by a sufficiently small space between the upper edge of the neck of the inner bubble and the upper part of the outer bubble, which then amounts to 1 to 3 mm.

The process according to the invention and the construction of the reaction equipment are illustrated in the attached figures.

FIG. 1 shows a diagram of the process for the continuous preparation of triacetin (glycide triacetate).

Figure 2:
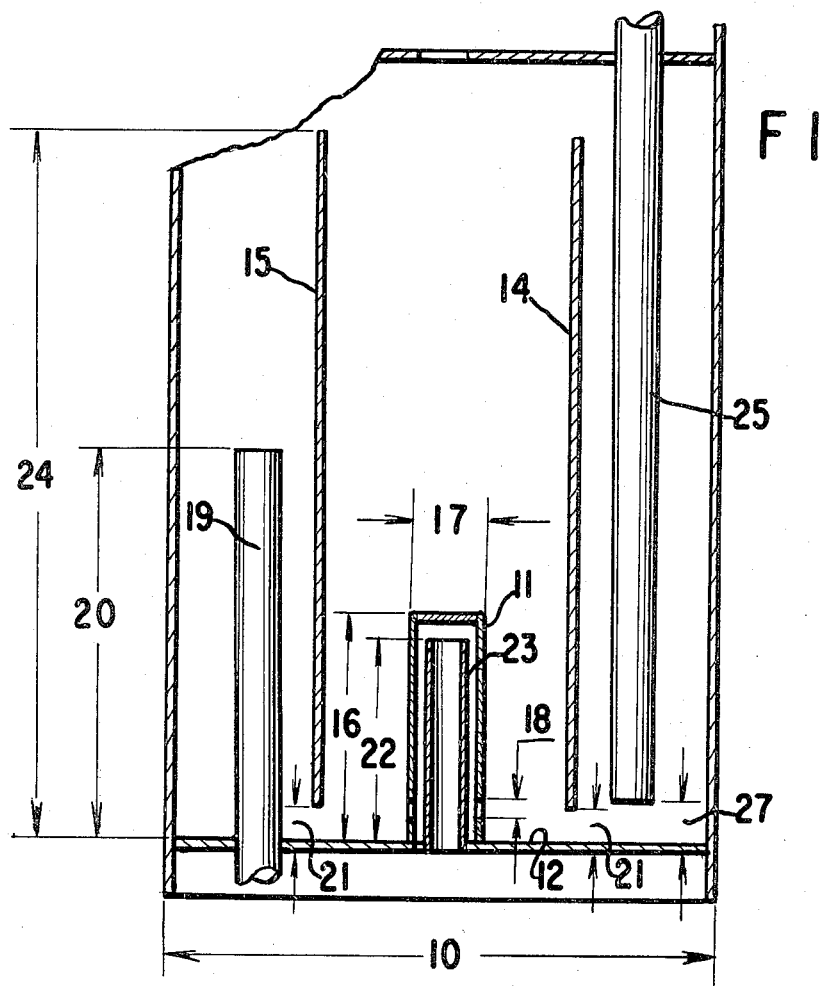
FIG. 2 shows a longitudinal section of a plate of a reactor which can be employed.

FIG. 2 shows a longitudinal section of a plate of the reactor.

Figure 3:
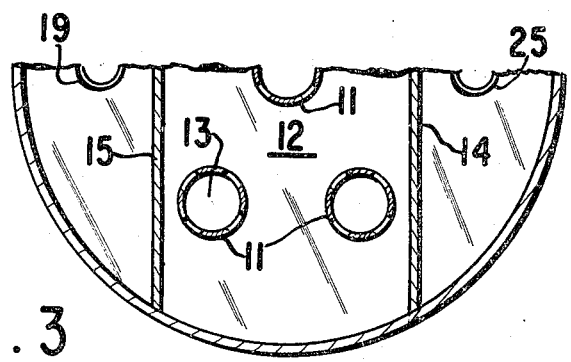
FIG. 3 shows a view from above of one half of a plate of the reactor.

FIG. 3 shows a view from above of ½ of a plate of the reactor.

Figure 4:
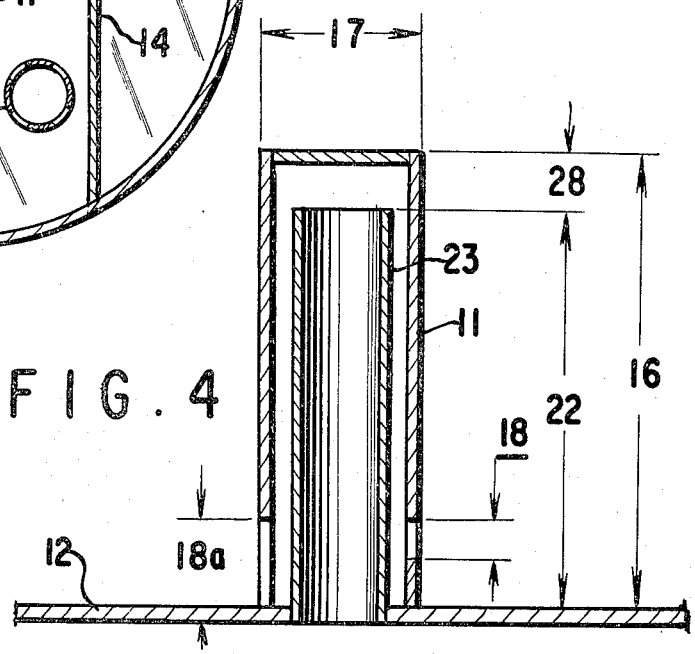
FIG. 4 shows an enlarged view of a bubble cap with two alternate gas exit ports.

FIG. 4 shows an enlarged view of a bubble cap with two alternate gas exit ports.

Figure 5:
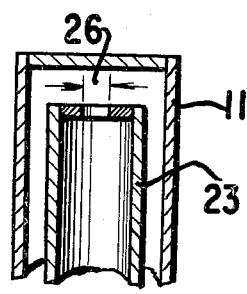
FIG. 5 shows an enlarged view of a bubble cap with a diaphragm inserted in the neck of the inner bubble.

FIG. 5 shows an enlarged view of a bubble cap with a diaphragm inserted in the neck of the inner bubble.

FIG. 6 shows a block flow diagram of one embodiment of the invention.

Figure 7:
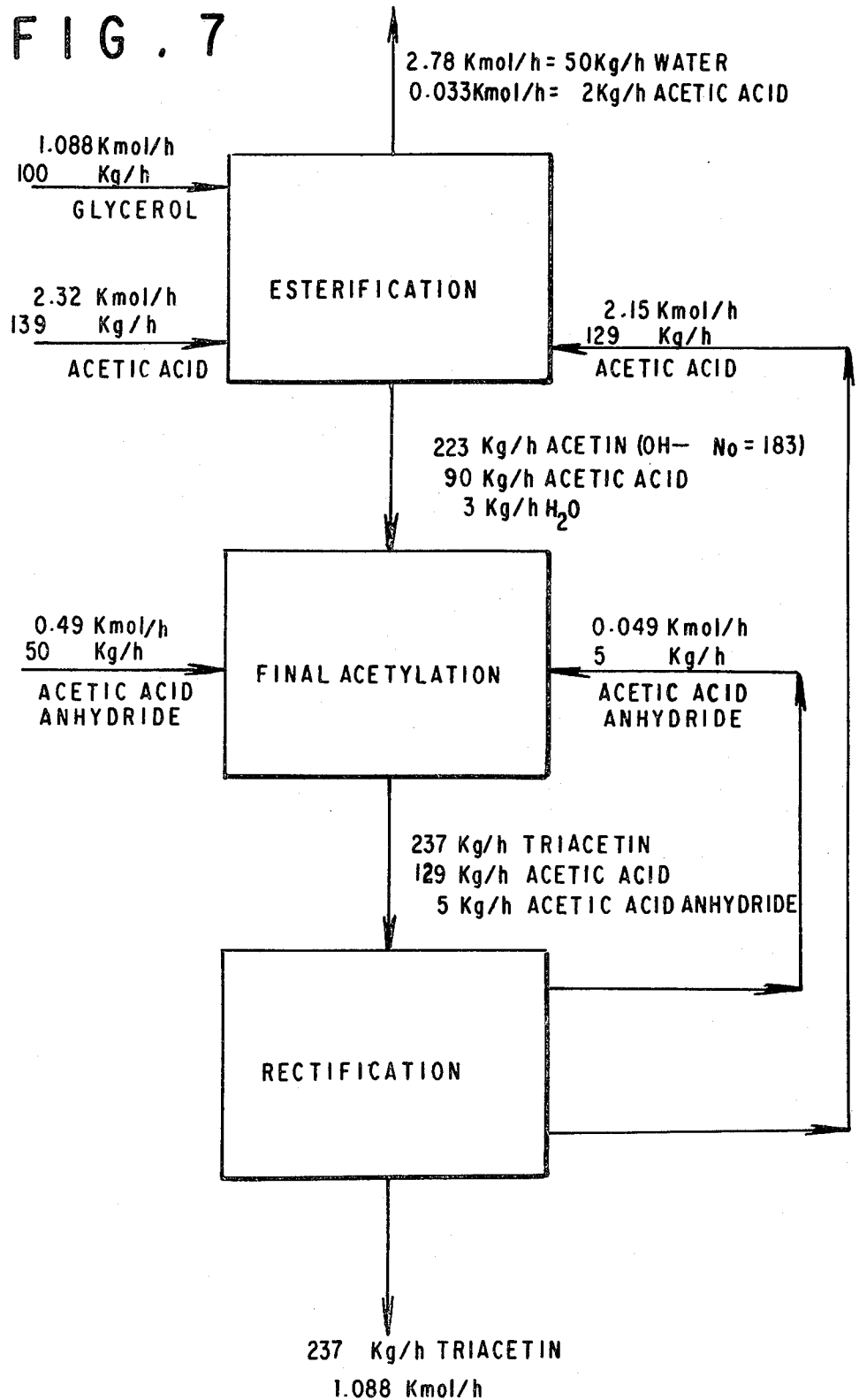
FIG. 7 shows a block flow diagram of another embodiment of the invention.

FIG. 7 shows a block flow diagram of another embodiment of the invention.

As shown in the skeletonized flow diagram of FIG. 1, glycerol is pumped from storage container B 3 with the aid of pump P 3, via a heat exchanger W 4, where it is heated to the reaction temperature, and transferred under the desired reaction pressure to the uppermost plate of reaction column K 1. Acetic acid is pumped from storage container B 1 with pump P 1, via vaporizer W 1 and superheater W 2 to beneath the bottom plate of reaction column K 1.

The glycerol transferred onto the uppermost plate, which may contain the catalyst, if desired, flows through reaction column K 1 in a counter-current flow to the ascending acetic acid vapor. The acetic acid reacts with the glycerol or with already formed monoacetin or diacetin, in dependence on the solubility of acetic acid in the liquid phase on the individual plates. Water, which is distributed between the liquid and the vapor due to the phase equilibrium, is formed in these reactions. The water content in the liquid phase on the plates decreases with increasing conversion (expressed, for example, by the decrease of the OH number) from the head to the sump of the column K 1, but it does not reach zero and counteracts the course of the various esterification reactions, especially the formation of triacetin, with water contents of up to 3% by weight in the liquid reaction mixture found at the bottom of the column K 1 or in the sump. This water content finally would bring the esterification to a halt via the adjustment of the reaction equilibrium. To prevent this, the invention calls for the feeding of acetic acid anhydride from storage container B 2 with the aid of pump P 2, via heat exchanger W 3, where it is heated to the reaction temperature, to a plate in the lower third of column K 1. This plate is chosen so that the glycerol coming from above has a total degree of esterification of about 70% or more, that is, an OH number of less than 600. The amount of the added acetic acid anhydride is such that the water dissolved at this point in the liquid reaction phase can be converted quantitatively into acetic acid and the monoacetin and diacetin present can be converted into triacetin. Relatively small amounts of acetic acid anhydride in the range of 0.1 to 1.5 mol per total molar amount of glycerol to be converted are needed for this purpose.

As an alternative, the final acetylation with acetic acid anhydride can be performed in a separate, second reactor. In this case, the sump products from the esterification column with an OH number of less than 600 are fed into the acetylation reactor together with acetic acid anhydride. The acetic acid formed during the acetylation is pumped into tank B 1 in this case, for further esterification. Suitable as secondary acetylation reactors are, for example, shorter bubble cap reactors comparable to K 1 or tube reactors filled with packing or cascades of agitator vessels.

The amount of acetic acid anhydride to be added in the individual case depends, on the one hand, on the degree of esterification which, in turn, depends on the contact time and thus on the dimensions of the utilized reaction column K 1 and on the other hand, on the amount of the molar ratio of the added acetic acid to glycerol.

The acetic acid anhydride fed into the lower third of reaction column K 1 or a second reactor of corresponding dimensions reacts with the water present in the liquid reaction phase and the water forming during the subsequent course of the esterification reactions and removes this from the equilibrium with the simultaneous formation of acetic acid. Part of the added acetic acid anhydride also reacts directly with the OH groups of the glycerol that are still not esterified, with the formation of acetic acid. The acetic acid formed during these two reactions is available for the esterification of glycerol, monoacetin and diacetin and is taken into consideration in the calculation of the amount of acetic acid to be added.

The head products collecting at the head of column K 1 are removed as superheated vapor and rectified in rectifier column K 2. The glycerol, monoacetin and possibly diacetin present in the head product are condensed in column K 2 and flow back into reactor K 1.

The head products which distill off and consist of the water of reaction and up to 3% by weight of acetic acid are condensed and supercooled in heat exchanger W 5, then reduced to atmospheric pressure via valve X 1 and drawn off via another heat exchanger W 7 into storage tank B 4. The amount of acetic acid contained in the distillate corresponds only to a minor part to the initially added molar excess of acetic acid. The runback transferred to column K 2 for separation is measured so that the superheating energy of the vapor flowing into column K 2 and the exothermy of the reaction on the uppermost plate of column K 1 are adequate for the vaporizing of the runback.

The reaction product is drained continuously from the sump of column K 1 or from the final acetylation reactor, cooled in heat exchanger W 6, its pressure is reduced via valve X 2 and it is piped into tank B 5. Depending on the conversion and the chosen reaction conditions, it contains from 20% to 40% by weight of acetic acid and from 1% to 5% by weight of acetic acid anhydride from the residue of the excess of acetic acid and/or acetic acid anhydride employed, in addition to triacetin as the desired product.

When the reaction is performed correctly, the reaction product contains only traces of glycerol, monoacetin, diacetin and water, so that the OH number normally lies below 1. Pure triacetin can be obtained readily by distillation in a rectification column of the obtained crude product, since, at atmospheric pressure, acetic acid boils at about 118° C., acetic acid anhydride boils at about 140° C., and glyceryl triacetate (triacetin) boils at about 258° C. Any catalyst that may still be present remains in the distillation residue.

According to the invention, the reaction column K 1 is designed in such a manner that the acetic acid formed in the final acetylation is converted during the esterification so that no excess of acetic acid is formed during the entire process. The water of reaction formed during the reaction is drawn off at the head of the column, and the column has the proper dimensions so that the acetic acid vapor rising in the column reacts with the OH groups of the glycerol and the water of reaction above the uppermost plate contains only from 1% to 3% by weight of acetic acid. After a neutralization, the head products can be transferred to a biologic clarifying vessel without any prior, expensive separation of the acetic acid from the water, which is necessary when higher concentrations of acetic acid are present in the head products.

There exist physico-chemical interrelations between the distribution of the reaction over the esterification and final acetylation phases that are presented schematically as follows. The block flow diagrams 1 and 2 (FIGS. 6 and 7) show the interrelations for a conversion of 70%, up to an OH number of 549 (FIG. 6), and a conversion of 90%, to an OH number of 183 (FIG. 7), in the esterification step.

Block flow diagram 1 (FIG. 6): 70% conversion in the esterification.

The given amounts are based on a feed of 100 kg/hr. of glycerol (OH number = 1,828) and production of 237 kg/hr. of triacetin. In the esterification column, the glycerol, introduced at the top, is esterified with 26 kg/hr. of fresh acetic acid and 200 kg/hr. of acetic acid formed from acetic acid anhydride during the final acetylation, to an esterification degree of 70% and an OH number of 549, based on the pure glycerol with a molar excess of 0.46 mol of acetic acid. According to the invention, the column is proportioned in such a manner that the water of reaction can be drawn off at the head of the column with a 3% by weight content of acetic acid maximum at a 70% conversion level. After neutralization, these head products then may be piped into a biologic clarifying vessel, for example, without the need for an expensive separation of the acetic acid from the water, which would be absolutely necessary at relatively high concentrations of acetic acid in the head products.

A 70% conversion in the esterification column with simultaneous maintaining of an acetic acid concentration of less than three percent in the head products at the reaction conditions that apply here, with temperatures between 180° and 250° C. and pressures of 3 to 30 bar in the absence of catalysts, or temperatures between 100° and 180° C. and pressures of 0.5 to 3 bar in the presence of catalysts, requires a contact time of the reactants on the column plates of at least one hour, distributed over at least 20 plates of special construction. Depending on the selected reaction conditions, the sump product of the esterification column still contains from 20% to 40% of acetic acid and 2% to 3% of water, in addition to the acetin (mono, di and tri) with an OH number of 549. This mixture is transferred to the final acetylation phase, which may be constructed as an extension of the esterification column or as a separate reactor.

An extension of the esterification column has the advantage that the acetic acid formed during the final acetylation by reaction of the acid anhydride with the remaining OH groups and with the reaction water contained in the sump product of the esterification column passes without working up into the esterification column. However, that final acetylation part of the esterification column has to be provided with a heating means for evaporation of a part of the acetic acid, as the reaction enthalpy of the exothermal final acetylation alone is not sufficient to evaporate the acetic acid.

During the final acetylation, the reaction mixture from the esterification phase is reacted with 145 kg/hr. (1.31 mol of anhydride per mol of glycerol) of fresh acetic acid anhydride to be converted and with 15 kg/hr. of acetic acid anhydride to be circulated as excess to form triacetin, that is, 1.44 mol of anhydride per mol of glycerol. The triacetin leaving the concurrent acetylation phase still contains acetic acid and anhydride that are separated in the separation step, from which the acetic acid is returned into the esterification and the excess anhydride into the final acetylation.

The final acetylation requires a contact time of at least 15 minutes, depending on the choice of reaction conditions of between 100° to 250° C. and 0.5 to 30 bar. This requires at least 5 additional reaction plates for the acetylation reaction integrated into the esterification column or a correspondingly proportioned reactor, that is, a cascade of agitator vessels or a tube reactor.

The respective total flow balance for the process at a 90% conversion in the esterification column can be seen in the block flow diagram 2 (FIG. 7). At otherwise identical reaction conditions, the reaction column must be extended by at least 10 plates to obtain the higher conversion while keeping the low acetic acid concentration in the head products. In contrast to the 70% conversion, the consumption of fresh acetic acid for the esterification now is 139 kg/hr., while only 129 kg/hr. are now produced via the anhydride; therefore, the esterification proceeds at an excess of 1.1 mol of acetic acid per mol of glycerol. In addition, less anhydride is used for the final acetylation, and the sump product of the esterification column contains only about 1% of water at a conversion of 90%, so that a considerably smaller amount of water has to be converted to acetic acid in the final acetylation phase.

Corresponding to the higher conversion rate in the esterification reaction, the contact time in the final acetylation phase is shorter, at otherwise identical reaction conditions, in comparison to a 70% conversion. This means that now only at least three reaction plates are needed for the acetylation reaction integrated into the esterification column or a correspondingly proportioned second reactor.

How the conversion is divided between the esterification and final acetylation is a matter of economics. A conversion rate below 65% to 70% in the esterification reaction is uneconomical since then more acetic acid is produced in the final acetylation phase than is used up in the esterification reaction. Therefore, conversions of at least 70% are to be attempted in the esterification reaction. Higher conversions can be achieved only by a corresponding extension of the contact time, such as, by more reaction plates. An increase in the excess acetic acid at the same contact time, that is, with the same number of plates, for example, results in an only insignificant increase of the conversion but lowers primarily the quality of the headproducts by an increase in the acetic acid concentration. On the other hand, the reaction rate of the final acetylation is considerably higher than that of the esterification, so that less reaction space is needed for the acetylation, which means fewer plates. Another consideration is the fact that acetic acid anhydride is more expensive than acetic acid. In the final analysis, the lowest possible production costs, including the costs of raw materials and investment, are a matter of optimal operating conditions.

The esterification according to the invention preferably takes place in a special bubble plate column K 1. A perfect functioning of the bubble plate at the high liquid levels necessary in the reaction column for obtaining the required contact time at simultaneously low vapor loads is produced by the construction, thanks to the double bubble principle. The double bubble consists of an inner bubble 23 (FIG. 4) for the adjustment of the dry pressure loss and an outer bubble 11 (FIG. 4) that takes care of the distribution of the vapor in the liquid. The inner bubble is also needed for the starting of the column so that the minimum liquid level on the plate can be adjusted in such a manner that the intake tube 25 (see FIG. 2) of the plate lying above is immersed in the liquid so that the vapor can only flow through the bubbles and not through the intake and outlet tubes of the plates when the column operation is started.

In a bubble plate column particularly suitable for the process according to the invention, as described with reference to FIG. 6, with at least 20 plates, the total area 13 occupied by the bubbles 11 (FIGS. 2, 3, 4, 5) on the plate 12 is 10% to 30% of the plate area lying between the intake weir 14 and the outlet weir 15, depending on the vapor charge. The ratio of height 16 of the bubbles 11 to the diameter 17 of the bubbles 11 is 0.5:1 to 3:1. In the bubbles 11, 4 to 12 orifices 18 with diameters of 2 to 6 mm are uniformly distributed along the periphery of the bubbles 11. These orifices 18 are located 5 to 10 mm above the plate 12. The penetration area through the orifices 18 for the vapor is 0.3% to 3% of the inside column cross-section. The height 20 of outlet tube 19 exceeds 80 mm. The height 22 of the inner bubble 23 is at least 20 mm greater than the distance 27 of the intake tube 25 from plate 12.

In an alternate construction of the bubbles 11 (FIG. 4), 4 to 12 vertical slits 18a with a width of 2 to 5 mm and a height of 5 to 15 mm are located close to plate 12 in bubble 11, instead of the orifices 18.

The height 24 of the intake and outlet weirs 14, 15 (FIG. 2) exceeds the height 20 of the outlet tube 19 that regulates the liquid level on plate 12. The weirs 14, 15 also have slits 21 close to plate 12. When the plate diameter 10 exceeds 300 mm, a reduced orifice 26 with a 3 to 15 mm diameter is provided in the neck of the inner bubble 23 (FIG. 5). The dry pressure loss due to this is at least twice the hydrostatic difference of the level of the liquid between intake and outlet and is at least 15 to 20 mm Water Column.

Another possibility to effect the required dry pressure loss is shown in FIG. 4. There the distance 28 between the upper edge of the neck of the inner bubble 23 and the outer bubble 11 is 2 to 6 mm.

The reaction can perhaps be better understood by consideration of the relative boiling points of the various ingredients as given in the following Table:

| Compound | B. P. at 760 mm unless otherwise indicated | |
|---|---|---|
| acetic acid | 118 | |
| acetic acid anhydride | 140 | |
| glycerol | 290 | |
| triacetin | 258 | |
| diacetin | 175 | 40 mm |
| monoacetin | 158 | 165 mm |

The following examples are illustrative of the practice of the invention without being limitative.

EXAMPLES

Example 1

A reaction column according to FIG. 1 with an inside diameter of 350 mm and 32 bubble plates corresponding to FIGS. 2, 3 and 4 were used to carry out the process. The volume available for the liquid reaction phase, based on the liquid without gas, was 400 liters.

A rectifying column K 2 was connected to the top of reaction column K 1, which was used to separate the glycerol and acetin from the vapor rising from the top plate of the reaction column K 1. The rectifying column K 2 was operated with a reflux ratio of approximately 0.2 so that the condensate from rectifying column K 2 contained only water of reaction and approximately 2% by weight of acetic acid.

The top plate of reaction column K 1 was charged with 176 kg/hr. (1.92 kmol/hr.) of glycerol of the quality DAB VII (OH-number 1,828) at a temperature of 250° C. and under a pressure of 7.5 bar. Below the 32$^{nd}$ plate of reaction column K 1, 326 kg/hr. (5.43 kmol/hr.) of acetic acid vapor heated to 250° C. (purity: 99.5% by weight acetic acid) were fed in. The molar ratio of acetic acid to glycerol thus was 2.83:1. An amount of 387 kg/hr. of reaction product consisting of 75% by weight of a mixture of monoacetin, diacetin and triacetin and containing 22% by weight of acetic acid and 3% by weight of water was removed from the sump of reaction column K 1.

A mean contact time of approximately one hour for the liquid reaction mixture is obtained with the given throughput rates.

The OH-number of the reaction product obtained was 549. The conversion, based on the amount of glycerol added, was thus 70%. This reaction product was acetylated with acetic acid anhydride to an OH-number of less than 0.1 in a second reactor.

The distillate draining from the condenser of rectifying column K 2 at a rate of 40 kg/hr. contained 98% by weight of water and 2% by weight of acetic acid. Only traces of glycerol and acetin were present.

Example 2

Analogous to Example 1, but in a column with 48 bubble plates, a sump product with an OH-number of 91.5 was obtained, i.e., a conversion of 95%. Again, 176 kg/hr. of glycerol were transferred to the top plate of the esterification column. Below the 48$^{th}$ plate, 463 kg/hr. (7.72 kmol/hr.) of superheated acetic acid vapor with a temperature of 250° C. was fed in. The molar ratio of acetic acid to glycerol was 4.01:1. The pressure in the column was again 7.5 bar, the reaction temperature was 250° C.

A sump product which consisted of 69.3% by weight of a mixture of diacetin and triacetin and contained 30% by weight of acetic acid and 0.7% by weight of water was drawn off from the sump of the esterification column at a rate of 442 kg/hr. This mixture was acetylated to an OH-number of <0.1 with acetic acid anhydride in a second reactor.

The distillate drawn off the column K 2 at a rate of 101 kg/hr. consisted mainly of water and contained about 3% by weight of acetic acid and traces of glycerol and acetin.

Example 3

The esterification was performed as in Example 1 in a column with 32 bubble plates, at a pressure of 7.5 bar and a reaction temperature of 250° C. The top plate was charged with 176 kg/hr. (1.92 kmol/hr.) of glycerol, while 326 kg/hr. (5.43 kmol/hr.) of superheated acetic acid vapor at 250° C. were fed in below the bottom plate and 166 kg/hr. (1.62 kmol/hr.) of acetic acid anhydride were fed in on the bottom plate. Besides this, 100 kg/hr. (0.97 kmol/hr.) of acetic acid anhydride were fed into a second reactor unconnected to the esterification column. The amount of acetic acid anhydride added per unit of time was such that the total amount of the water that was dissolved in the sump product at the 70% conversion according to Example 1 as well as the water that was to be expected from the esterification of the free OH-groups of the glycerol still present, could react quantitatively to form acetic acid. In addition, an excess of 10% is included in the share of acetic acid anhydride, which is returned either directly or after a separation from the acetic acid in a separating apparatus.

The molar ratio of acetic acid to glycerol was 2.83:1, the corresponding ratio of acetic acid anhydride to glycerol was 1.35:1.

The reaction mixture drawn off from the sump of the reaction column has an OH number of 74, that is, a conversion of 96%, based on the glycerol, was obtained. This reaction mixture was mixed with 100 kg/hr. of acetic acid anhydride and fed into a tube reactor as second reactor in which the reaction continued to an OH number of <0.1.

At the head of column K 2, the water of reaction was drawn off that still contained 2.5% by weight of acetic acid and was transferred into a biologic clarifying vessel after neutralization.

EXAMPLE 4

In a reaction column as in Example 1, but with 42 plates, operating at a pressure of 7.5 bar and a reaction temperature of 250° C., the top plate was charged with 176 kg/hr. (1.92 kmol/hr.) of glycerol, which reacted with the 326 kg/hr. (5.43 kmol/hr.) of superheated acetic acid vapor fed in below the 32nd plate and the 266 kg/hr. (2.59 kmol/hr.) of acetic acid anhydride preheated to the reaction temperature fed into the 32nd plate. The molar ratio of acetic acid to glycerol was 2.83:1, the corresponding ratio of acetic acid anhydride to glycerol was 1.35:1.

The amount of acetic acid anhydride that was added during a unit of time was such that, on the one hand, the total amount of the water that was dissolved in the reaction mixture on the 32nd plate, and that which was to be expected from the esterification of the free OH groups of the glycerol still present, on the other hand, could be converted quantitatively into acetic acid. In addition, the amount of acetic acid anhydride included an excess of 10%, which was returned to the process directly or after separation of the acetic acid in a preparation plant.

From the sump of the column was withdrawn a reaction mixture which contained, in addition to acetic acid and acetic acid anhydride, triacetin with an OH number of <0.1. The sump of the column was designed as an evaporator, so that a part of the acetic acid dissolved in the sump was evaporated, which then rose in the column, effecting the necessary mixing on the bottom bubble plates 42 to 33.

The reaction water which still contained 2.5% by weight of acetic acid was withdrawn at the head of column K 2. After neutralization, the head product was conducted to a biological clarification plant.

Example 5

In a reaction column, as in Examples 1 and 4, but with 54 reaction bubble plates, 176 kg/hr. (1.92 kmol/hr.) of glycerol were charged in at the top plate. Under the 48th plate, 463 kg/hr. (7.72 kmol/hr.) of superheated acetic acid vapor were fed. On the 48th plate 41 kg/hr. (0.40 kmol/hr.) of acetic acid anhydride, preheated to the reaction temperature, were added to the reaction mixture. The molar ratio acetic acid: glycerol was 4.02:1, the corresponding ratio of acetic acid anhydride: glycerin=0.21:1. The amount of acetic acid anhydride fed per unit of time was so selected that, on the one hand, the total amount of water which was dissolved in the reaction mixture on the 48th plate could be reacted quantitatively to give acetic acid and which, on the other hand, could be required for the esterification of the still present free OH groups of the glycerol. In addition, an excess of 10% is included in the amount of acetic acid anhydride, which is returned into the process either directly or after a separation of the acetic acid in a separating apparatus.

A reaction mixture that contained triacetin with an OH number of <0.1 as well as acetic acid and acetic acid anhydride was drawn off from the sump of the column. The sump of the column was constructed as an evaporator that evaporated part of the acetic acid dissolved in the sump, which then rose upward in the column and took care of the necessary mixing on plates 54 to 49.

The water of reaction, which still contained 2.5% by weight of acetic acid, was drawn off at the head of column K 2. After neutralization, the head products were piped into a biologic clarifying vessel.

Example 6

Analogous to Example 1 and operating under a pressure of 1.5 bar, 167 kg/hr. (1.92 kmol/hr.) of glycerol of the quality DAB VII (OH number 1,828) and a temperature of 150° C. were fed into the top plate of reaction column K 1. The glycerol contained 0.5% by weight of p-toluene-sulfonic acid as catalyst. Below the 32nd plate of reaction column K 1, 326 kg/hr. (6.43 kmol/hr.) of acetic acid vapor heated to 150° C. (purity 99.5% by weight of acetic acid) were fed in. The molar ratio of acetic acid to glycerol was therefore 2.83:1. Crude acetin with an OH number of 311, corresponding to a conversion of 83%, based on the glycerol, was removed from the sump of K 1. The sump product still contained about 1% of water in addition to 24% of acetic acid.

The sump product from K 1 was acetylated to an OH number of <0.1 with acetic acid anhydride in a second reactor.

The distillate draining from the condenser of the rectifying column K 2 contained 98% by weight of water and 2% by weight of acetic acid. Traces of glycerol and acetin could be identified as well.

The preceding specific embodiments are illustrative of the practice of the invention. It is to be understood, however, that other expedients known to those skilled in the art or disclosed herein, may be employed without departing from the spirit of the invention or the scope of the appended claims.

We claim:

1. A process for the continuous production of triacetin consisting essentially of continuousy charging liquid glycerol into a first liquid reaction area through which acetic acid vapors and water vapors flow, said liquid reaction area being divided into a number of separate individual areas through which liquid glycerol and liquid acetin reaction products flow in one direction and gaseous acetic acid and water flow in a countercurrent direction, continuously charging acetic acid vapor to a separate individual area where said liquid mixture has an OH number of less than 600, said liquid reaction areas being maintained at a pressure of from 0.2 to 30 bar and a temperature of from 100° to 250° C., the number of said separate individual areas and the amount of liquid glycerol and gaseous acetic acid charged being so selected that the total contact time of the reactants is at least one hour, continuously separating a liquid mixture of acetins and water having an OH number of less than 600, continuously passing said liquid mixture into a second liquid reaction area, continuously adding thereto liquid acetic acid anhydride in an amount sufficient to react with water dissolved in said liquid mixture to form acetic acid and to react with monoacetin and diacetin present to form triacetin, continuously recoverng triacetin, continuously passing vaporized acetic acid formed into said separate individual area where said liquid mixture has an OH number of less than 600, and continuously recovering a mixture of water vapors and acetic acid vapors having a content after condensation of less than 3% by weight of acetic acid.

2. The process of claim 1 wherein said continuous production of triacetin occurs in the absence of a catalyst at a pressure of from 3 to 30 bar and a temperature of 180° to 250° C.

3. The process of claim 1 wherein said continuous production of triacetin occurs in the presence of an acid esterification catalyst at a pressure of from 0.2 to 3 bar and a temperature of from 100° to 180° C.

4. The process of claim 3 wherein said acid esterification catalyst is employed in an amount of from 0.01% to 0.5% by weight, based on the amount of glycerol charged.

5. The process of claim 3 or 4 wherein said acid esterification catalyst is p-toluene sulfonic acid.

6. The process of claim 1 or 2 or 3 or 4 wherein said second liquid reaction area is divided into a number of separate individual areas and is a continuation of said first liquid reaction area.

7. The process of claim 6 wherein said second liquid reaction area is charged with said liquid acetic acid anhydride in the lower third of the total first and second liquid reaction areas, said liquid acetic acid anhydride and said liquid mixture of acetins and water having an OH number of less than 600 flowing concurrently through said number of separate individual areas in said second liquid reaction area.

8. The process of claim 1 wherein said second liquid reaction area is separate from said first liquid reaction area.

9. The process of claim 1 or 2 or 3 or 4 wherein the molar ratio of acetic acid to glycerol charged is 2.5:1 to 5:1.

10. The process of claim 1 or 2 or 3 or 4 wherein the molar ratio of acetic acid anhydride to glycerol charged is 0.1:1 to 1.5:1.

* * * * *